United States Patent [19]
Tovey et al.

[11] Patent Number: 5,411,519
[45] Date of Patent: May 2, 1995

[54] SURGICAL APPARATUS HAVING HINGED JAW STRUCTURE

[75] Inventors: H. Jonathan Tovey, Milford; Paul A. Scirica, East Hampton, both of Conn.

[73] Assignee: United States Surgical Corporation, Norwalk, Conn.

[21] Appl. No.: 949,576

[22] Filed: Sep. 23, 1992

[51] Int. Cl.⁶ .............................................. A61B 17/28
[52] U.S. Cl. ..................................... 606/207; 128/751
[58] Field of Search ........................ 606/205–211, 606/51, 52, 170, 174; 128/4, 6, 751–755; 81/90.2, 387

[56] References Cited

U.S. PATENT DOCUMENTS

| | | | |
|---|---|---|---|
| 2,807,710 | 5/1950 | Grosso | 606/208 |
| 4,572,185 | 2/1986 | Rich . | |
| 4,944,471 | 7/1990 | Hasson | 606/207 |
| 5,047,046 | 9/1991 | Bodoia . | |
| 5,113,846 | 5/1992 | Hiltebrandt et al. . | |
| 5,156,633 | 10/1992 | Smith . | |
| 5,174,300 | 12/1992 | Bales et al. | 128/751 |
| 5,176,699 | 1/1993 | Markham | 606/208 |
| 5,282,826 | 2/1994 | Quadri | 606/207 |

*Primary Examiner*—Stephen C. Pellegrino
*Assistant Examiner*—William Lewis

[57] ABSTRACT

A surgical apparatus is provided which includes a handle portion, an endoscopic portion extending longitudinally from the handle portion, and a pair of articulating jaw members each having first and second relatively articulatable sections movable between a contracted position and a deployed position. A tubular member is associated with the endoscopic portion of the instrument and is movable along the longitudinal axis thereof between a proximal position spaced from the jaw members and a distal position substantially enclosing the jaw members and maintaining them in their contracted position.

36 Claims, 8 Drawing Sheets

SURGICAL APPARATUS HAVING HINGED JAW STRUCTURE

BACKGROUND OF THE INVENTION

1. Field of the Invention

The subject invention relates to surgical apparatus for performing endoscopic and laparoscopic surgical procedures, and more particularly, to surgical apparatus having articulable jaw structure.

2. Description of the Related Art

In endoscopic and laparoscopic surgical procedures, a small incision or puncture is made in the patient's body to provide access for a trocar or cannula device. Once extended into the patient's body, the cannula allows insertion of various surgical instruments such as dissectors, scissors, forceps, or graspers. In the past, the configuration of these surgical instruments has been limited to those having jaw structure which is capable of unobstructed passage through the cannula. Moreover, it has been necessary for these instruments to have substantially longitudinally extending jaw configurations which can be inserted through the trocar housing and cannula device.

There exists however, a variety of surgical instruments having a jaw structure which is poorly suited for insertion through a cannula during endoscopic or laparoscopic procedures. These instruments, which include mixter-type forceps and varco-type forceps, have irregular jaw configurations useful in performing various surgical procedures. Specifically, these devices have cooperating jaws which depend either angularly or arcuately from the longitudinal axis of the instrument, making passage through a cannula virtually impossible. Consequently, there exists a need in the art for instruments having jaw configurations such as these which may be utilized in endoscopic or laparoscopic procedures.

It is desirable therefore, to provide an endoscopic surgical instrument having angularly or arcuately configured jaw members adapted for insertion through a trocar or cannula device, and more particularly, to provide an instrument having articulable jaw structure adapted for insertion through a cannula device during endoscopic or laparoscopic surgical procedures.

SUMMARY OF THE INVENTION

The subject invention provides a novel surgical instrument having an angularly or arcuately shaped jaw structure which is adapted and configured for unobstructed insertion through a trocar housing and cannula device during endoscopic or laparoscopic procedures.

The surgical apparatus of the subject invention in accordance with one embodiment comprises a handle portion having a fixed handle, a pivoting handle, and a barrel. An elongated endoscopic portion extends from the barrel of the handle portion, and articulating tool means are operatively associated with a distal end of the endoscopic portion of the instrument. The articulating tool means includes a pair of opposed cooperating jaw members each having first and second relatively articulatable sections movable between a contracted position and a normally biased deployed position. Preferably, the instrument is provided with a tubular member associated with the endoscopic portion thereof, and movable along its longitudinal axis between a proximal position spaced from the jaw members and a distal position substantially enclosing the jaw members and maintaining them in their contracted position. A spring member is provided for biasing the relatively articulable sections into their deployed position. The spring member may comprise an elongated leaf spring, a looped torsion spring, or a coiled spring.

The surgical instrument of the subject invention further comprises means associated with the handle portion thereof for moving the cooperating jaw members between a normally open position and a closed position, and means for selectively locking the cooperating jaw members in a desired position. Means are also provided for inhibiting the egress of insufflation gas from the operative site, for rotating the endoscopic portion of the instrument about its longitudinal axis relative to the handle portion, and for performing electro-cauterization at the tool means.

Further features of the endoscopic surgical apparatus of the subject invention will become more readily apparent from the following detailed description of the invention.

BRIEF DESCRIPTION OF THE DRAWINGS

Preferred embodiments of the subject invention will be described hereinbelow with reference to the drawings, wherein:

FIGS. 10-12 illustrate a sequential deployment of an articulable jaw member in accordance with a preferred embodiment of the subject invention wherein:

DETAILED DESCRIPTION OF THE PREFERRED EMBODIMENTS

It is generally accepted that endoscopic procedures are more common than laparoscopic procedures. Accordingly, the subject invention shall be discussed in terms of endoscopic procedures and apparatus. However, use herein of terms such as "endoscopic", "endoscopically", and "endoscopic portion", among others, should not be construed to limit the present invention to an apparatus for use only in conjunction with an endoscopic tube. To the contrary, it is believed that the subject invention may find use in any procedure in which access is limited to a small incision, including but not limited to laparoscopic procedures.

In the drawings and the description which follows, the term "proximal" will refer to the end of the apparatus which is closest to the operator while the term "distal" will refer to the end which is furthest from the operator.

Figure 1:
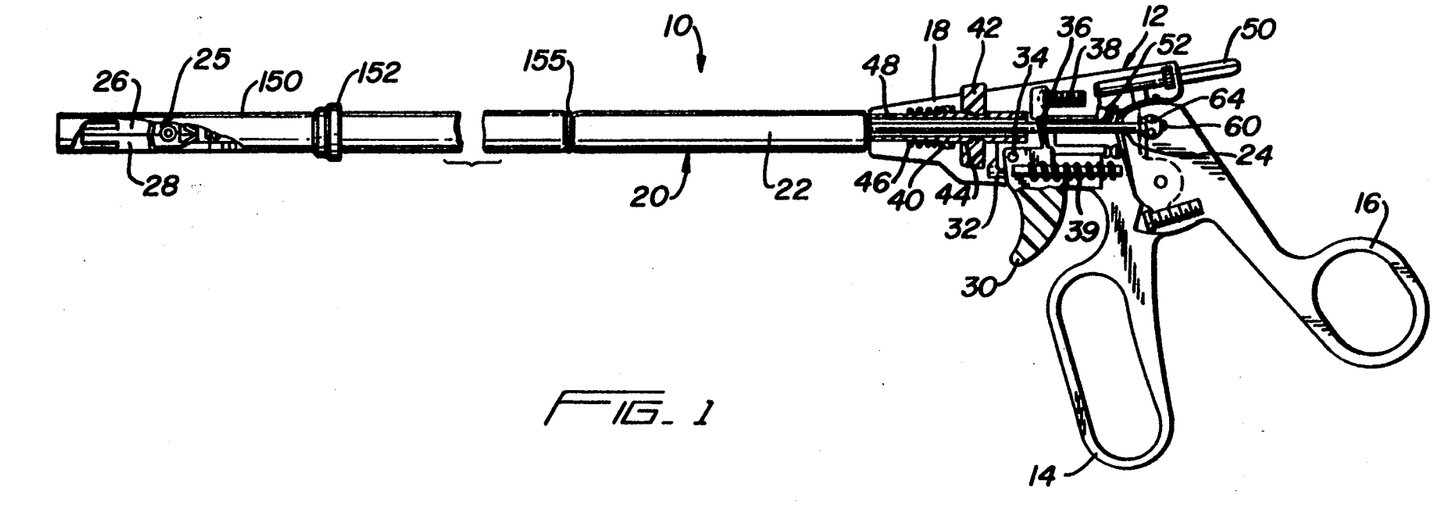
FIG. 1 is a side elevational view of a surgical apparatus in accordance with a preferred embodiment of the subject invention with the handle portion thereof shown in cross-section, and the distal end thereof cut-away to illustrate the structure of the jaws of the instrument.

Referring now in detail to the drawings in which like reference numerals identify similar or identical elements, a preferred embodiment of the surgical apparatus of the subject invention is illustrated in FIG. 1, and is designated generally by reference numeral 10. Surgical apparatus 10 comprises a handle portion 12 defining a fixed handle 14, a pivoting handle 16, and a barrel portion 18. An elongated endoscopic portion 20 extends from the barrel portion 18 of handle portion 12 and includes an elongated outer tube 22, and a coaxial internal control shaft 24. Control shaft 24 is adapted to reciprocate longitudinally within the endoscopic portion 20 of surgical apparatus 10 in response to manipulation of the pivoting handle 16 to operate a tool mechanism 25 which is operatively associated with a distal end of endoscopic portion 20. Tool mechanism 25 comprises a pair of cooperating jaw members 26 and 28 which may be configured in the form of scissors, graspers, forceps, or dissectors. However, a preferred embodiment of the tool mechanism 25 will be described herein with respect to a pair of cooperating jaw members configured as a forceps device.

The handle portion 12 of surgical apparatus 10 is provided with an assembly for selectively locking the cooperating jaw members 26 and 28 of tool mechanism 25 in a desired position through operative association with the internal control shaft 24. See, commonly assigned U.S. application Ser. No. 07/863,951, the disclosure of which is incorporated herein by reference. The locking assembly includes a trigger 30 interconnected to a brake member 32 which is adapted to pivot about a pin 34 in response to manipulation of trigger 30, and which is provided with a circular aperture 36 through which control shaft 24 extends. A spring biased plunger 38 is disposed in the barrel portion 18 of handle 12 and is adapted to urge the brake member 32 in a distal direction. A spring biased rod 39 is also disposed in barrel portion 18 for biasing trigger 30 in a distal direction corresponding to the jaw members 26 and 28 of tool mechanism 25 being in a normally open position.

Figure 2:
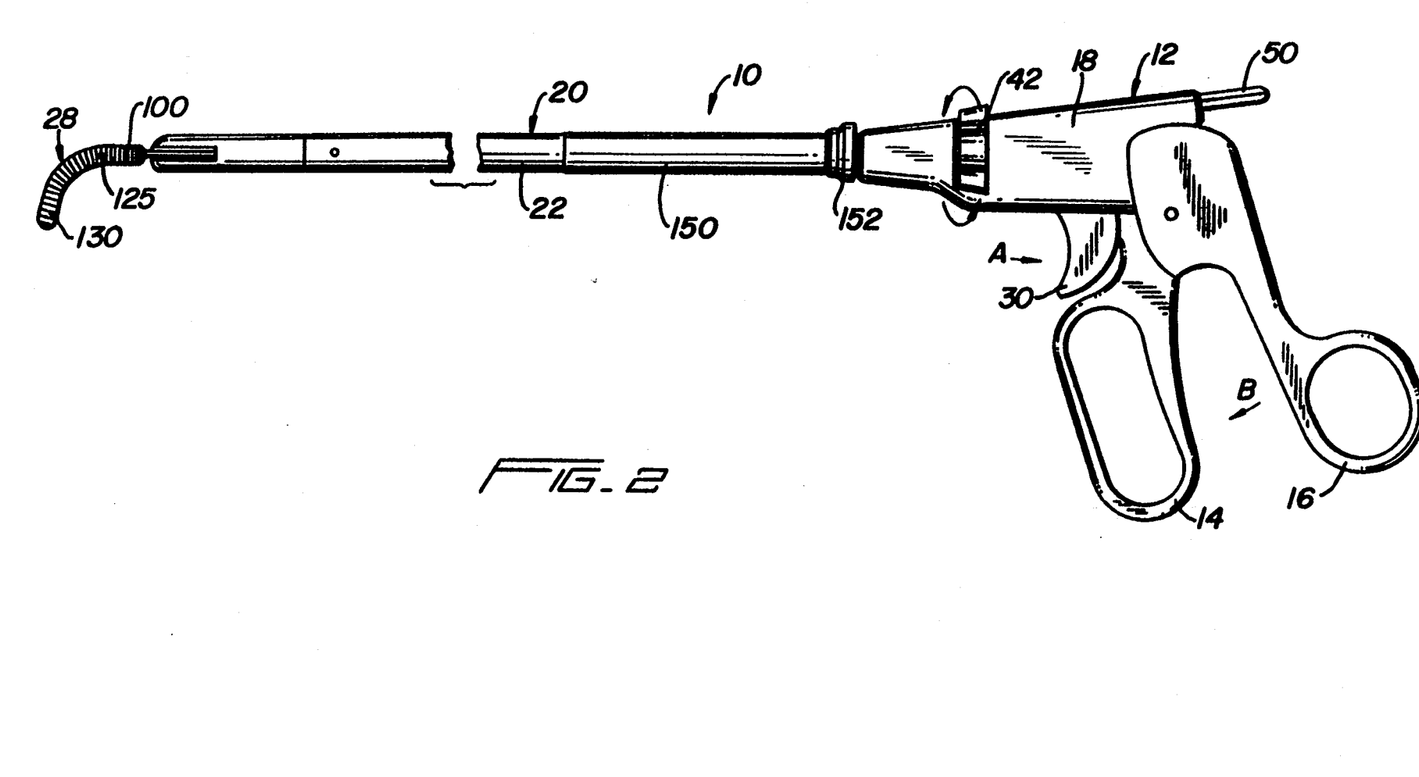
FIG. 2 is a side elevational view of the endoscopic surgical apparatus of FIG. 1, with the endoscopic portion thereof rotated 90° about the longitudinal axis thereof, illustrating the articulable jaw members of the instrument in a fully deployed and closed position.

Referring to FIG. 2, proximal movement of trigger 30 in the direction of arrow "A" allows the brake member 32 to pivot in a distal direction under the influence of the spring biased plunger 38 such that the aperture 36 in brake member 32 becomes eccentric with respect to the longitudinal axis of control shaft 24. This eccentricity causes the control shaft 24 to be fictionally retained in a selected longitudinal position. However, manipulation of the pivoting handle 16 of handle portion 12 in the direction of arrow "B" will be unencumbered since brake member 32 is free to move in a proximal direction against the spring biased plunger 38.

Surgical apparatus 10 further comprises a mechanism for rotating the endoscopic portion 20 about its longitudinal axis relative to handle portion 12 to increase the range of operability of the instrument. This mechanism comprises an annular bushing 40 which is concentrically mounted within a rotatable collar 42. Collar 42 is mounted within a chamber 44 defined in the barrel portion 18 of handle 12 and bushing 40 is maintained against collar 42 by a coiled spring 46 which acts to bias bushing 40 towards the proximal end of the instrument. The proximal end of a tubular extension member 48 is engaged within bushing 40 and the distal end thereof is engaged in the outer tube 22 of endoscopic portion 20 to facilitate rotation of endoscopic portion 20 relative to the handle portion 12 of the instrument.

The surgical apparatus 10 of the subject invention may also be used for electro-cautery purposes in addition to its grasping features. For this purpose, a plug adaptor 50 extends proximally from the barrel portion 18 of handle 12 to provide a connection for use in electro-cauterization procedures at the surgical site. A contact spring 52 is disposed in handle portion 12 for electrically connecting the plug adaptor 50 to control shaft 24 which transmits electrical current to the tool mechanism 25 at the distal end of the instrument. In order to protect the surgeon who is using the device from electrical shock during cauterization procedures, the handle portion 12 of surgical apparatus 10 is preferably constructed of a rigid non-conducting material which renders the apparatus light weight and electrically insulated. In addition, the outer tube 22 of endoscopic portion 20 is provided with an insulating coating to further protect the surgeon from electrical shock, while preventing damage to surrounding tissue.

To facilitate cooperative movement of the opposed jaw members 26 and 28 of tool mechanism 25, the control shaft 24 is formed with an annular tail 60 at the proximal end thereof, which is engaged in a locking clip 64 operatively mounted in the pivoting handle 16 of handle portion 12. Thus, pivotal movement of pivoting handle 16 will cause control shaft 24 to translate in an axial direction, transmitting longitudinal motion to the cooperating jaw members 26 and 28 of tool mechanism 25.

Figure 3:
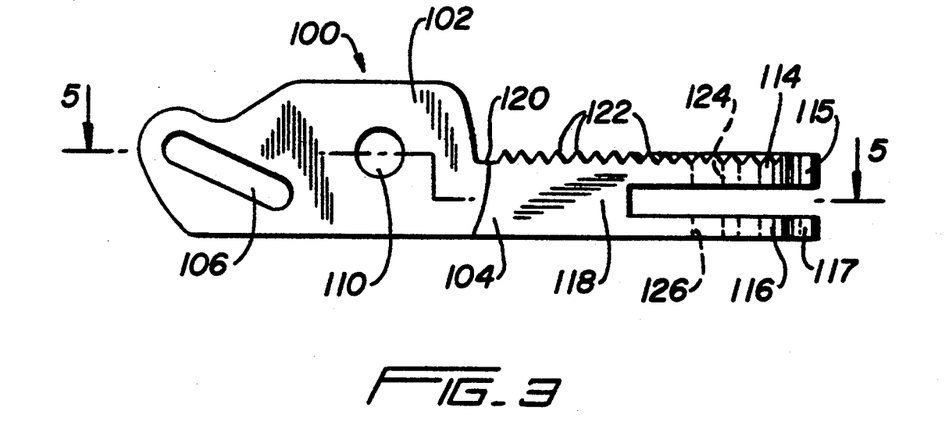
FIG. 3 is a side elevational view of the proximal portion of the articulable jaw structure of the subject invention.
Figure 4:
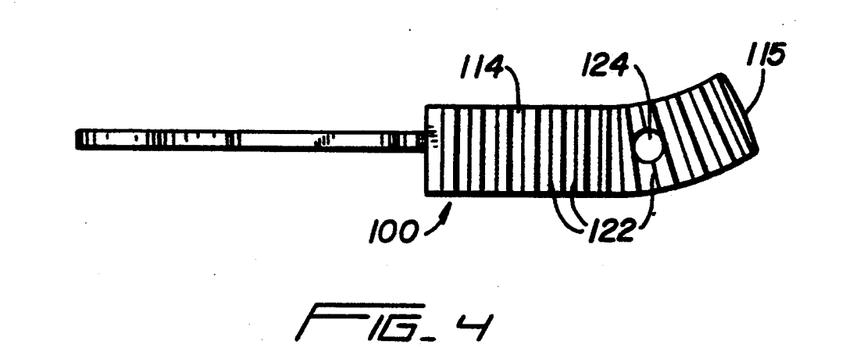
FIG. 4 is a top plan view of the proximal portion of the articulable jaw structure of FIG. 3.
Figure 5:
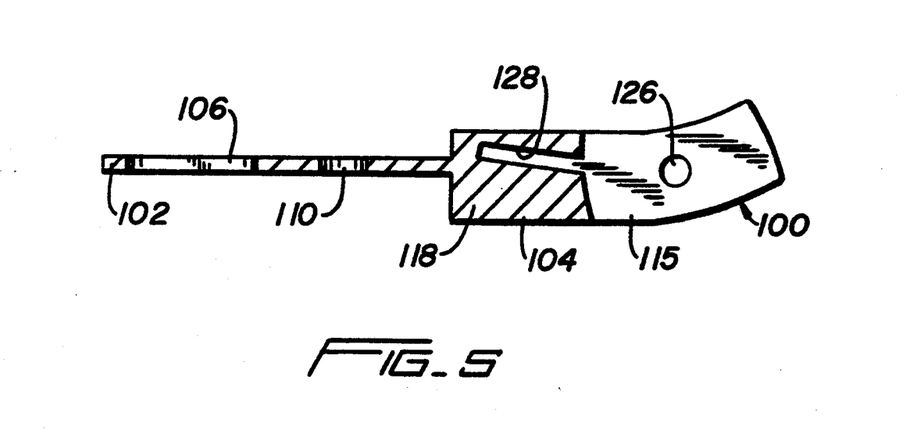
FIG. 5 is a cross-sectional view, taken along line 5—5 of FIG. 3.
Figure 6:
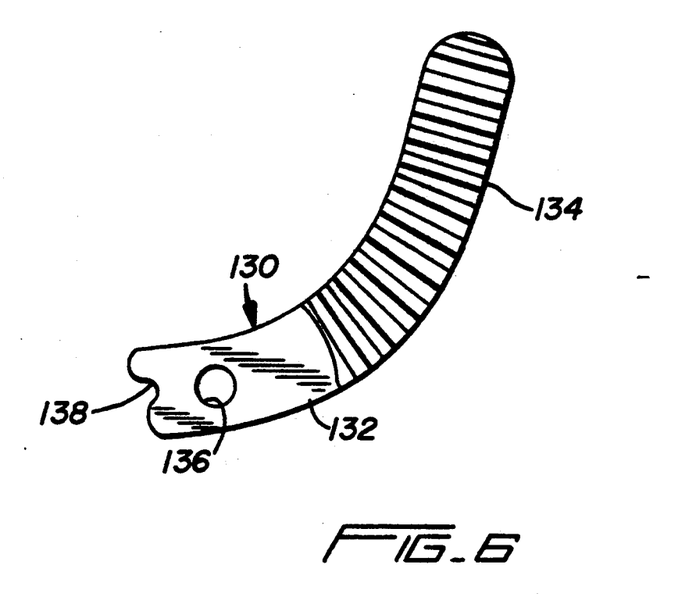
FIG. 6 is a top plan view of the distal portion of the articulable jaw structure of the subject invention.
Figure 7:
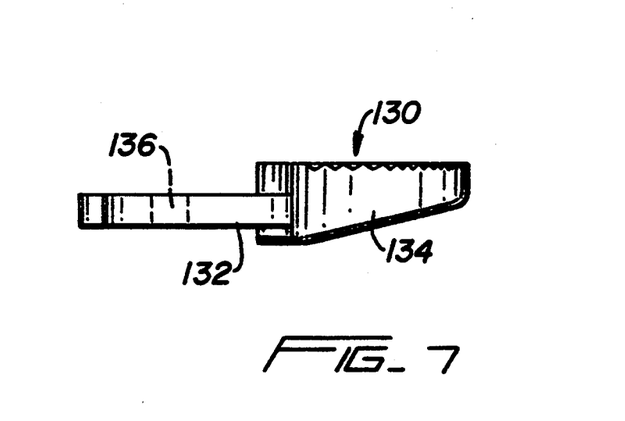
FIG. 7 is a front elevational view of the distal portion of the articulable jaw structure of FIG. 6.
Figure 8:
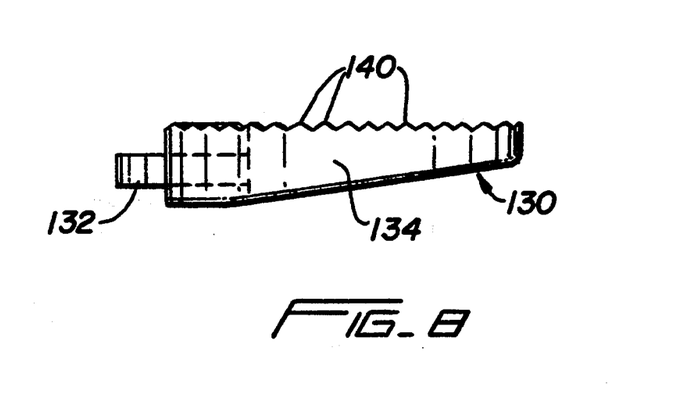
FIG. 8 is a side elevational view of the distal portion of the articulable jaw structure of FIG. 6.

Referring to FIGS. 2-8, each jaw of tool mechanism 25 is defined by two relatively articulable sections hinged to one another and including a proximal section 100 and a distal section 130. Proximal section 100 comprises a flange portion 102 and a transverse clevis portion 104. The flange portion 102 of each jaw is provided with an angularly disposed cam slot 106 and an adjacent pivot aperture 110. To achieve cooperative movement of jaw members 26 and 28, the cam slot 106 in jaw member 26 is disposed at an angle complimentary to the angle at which the cam slot in jaw member 28 is disposed. A cam pin 108 is associated with the complimentary cam slot 106 in each jaw, and a pivot pin 112 is associated with pivot aperture 110 (See FIG. 9). Cam pin 108 is operatively connected to the end of control shaft 24 for camming the cooperating jaws 26 and 28 between a normally open position and a closed position in response to axial movement of control shaft 24. As best seen in FIG. 3, the clevis portion 104 of proximal section 100 includes upper and lower spaced apart shackles 114 and 116 having arcuate distal end portions 115 and 117 respectively depending from the longitudinal axes thereof, and a body 118. The external surface 120 of upper shackle 114 is provided with a plurality of spaced apart serrations 122 each having a substantially triangular cross-sectional configuration for gripping tissue or organs within the abdominal cavity. Apertures 124 and 126 extend through the opposed shackles 114 and 116 for receiving a barrel pin 125 (see for example, FIG. 10) which is also associated with the distal section 130 of each of the articulable jaws of tool mechanism 25. A generally elongated cavity 128 is defined in the body 118 of clevis portion 104 for maintaining structure adapted for biasing the relatively articulable proximal and distal section 100 and 130 of each of the jaw members 26 and 28 in their deployed position, which will be discussed in greater detail hereinbelow.

The distal section 130 of each of the opposed jaw members 26 and 28 of tool mechanism 25 comprises a mounting portion 132 and a body portion 134 which together define a substantially arcuate structure. In particular, the curvature of the mounting portion 132 is substantially identical to the curvature of the distal end portions 115 and 117 of the shackles 114 and 116 of clevis portion 104. Thus, when jaws 26 and 28 are in their fully deployed position, the proximal section 100 and the distal section 130 will define a substantially continuous arcuate or crescent shaped configuration which is advantageous for use in endoscopic surgical procedures. The mounting portion 132 of distal section 130 is provided with an aperture 136 which corresponds to the respective apertures 124 and 126 in the opposed shackles 114 and 116 of proximal section 100 for accommodating barrel pin 125. A notched region 138 is defined in the proximal end of mounting portion 132 for operatively engaging the biasing structure discussed briefly above. In addition, the upper surface of the body portion 134 of distal section 130 is provided with a plurality of spaced apart transverse serrations 140 of triangular cross-sectional configuration substantially identical to those provided on shackle 114. However, the serrations disposed in the arcuate region of body portion 134 are arranged in a radial manner as if extending from a common geometric center point.

Figure 10:
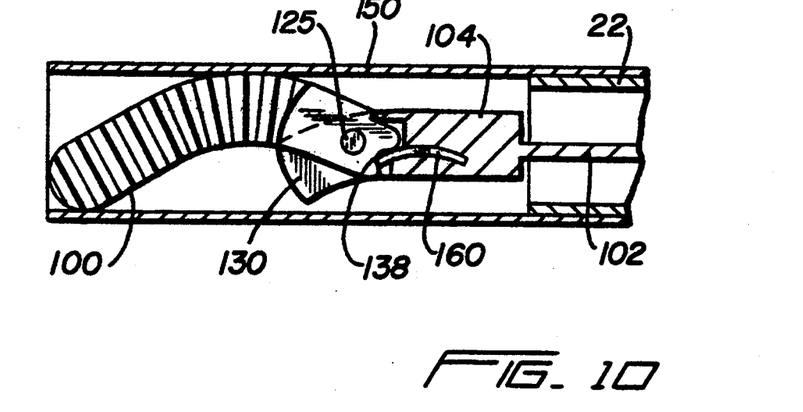
FIG. 10 shows the articulable jaw member in a contracted position enclosed within a tubular housing.
Figure 11:
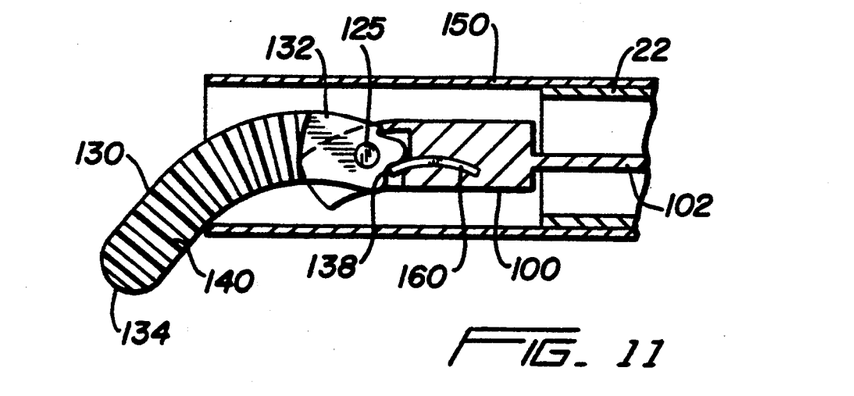
FIG. 11 shows the articulable jaw member in a partially deployed position as the tubular housing is withdrawn.
Figure 12:
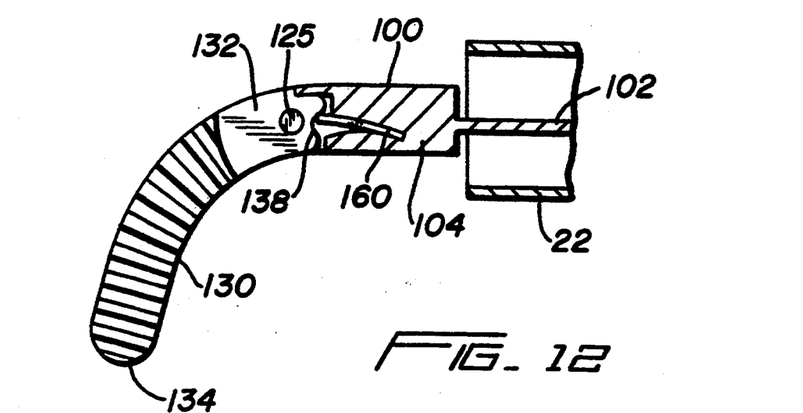
FIG. 12 shows the articulable jaw member in a fully deployed position.
Figure 15:
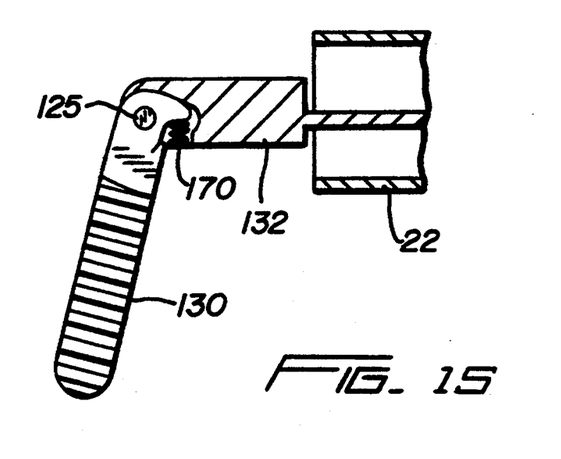
FIG. 15 is a side elevational view, partially cut-away, of an alternate embodiment of an articulable jaw member in a fully deployed position.

The articulating jaws 26 and 28 of tool mechanism 25 are normally biased in a fully deployed position with each jaw defining a substantially arcuate configuration, although, as illustrated in FIG. 15, the jaws may have a substantially angular configuration in their deployed position. Thus, to facilitate their insertion through a trocar or cannula device the jaws are moved from their normally deployed position to a substantially contracted position. Referring to FIGS. 10-12, to achieve such a configuration an elongated tubular housing 150 having an annular flange 152 at its proximal end is provided and is manually movable coaxially along the length of the endoscopic portion 20 of apparatus 10. The tubular housing 150 encloses and maintains the relatively articulable proximal and distal sections 100 and 130 of each of the articulating jaw members 26 and 28 of tool mechanism 25 in their contracted position wherein the distal section 130 of each of the jaws is substantially coplanar with the proximal section 100 of each jaw.

Figure 9:
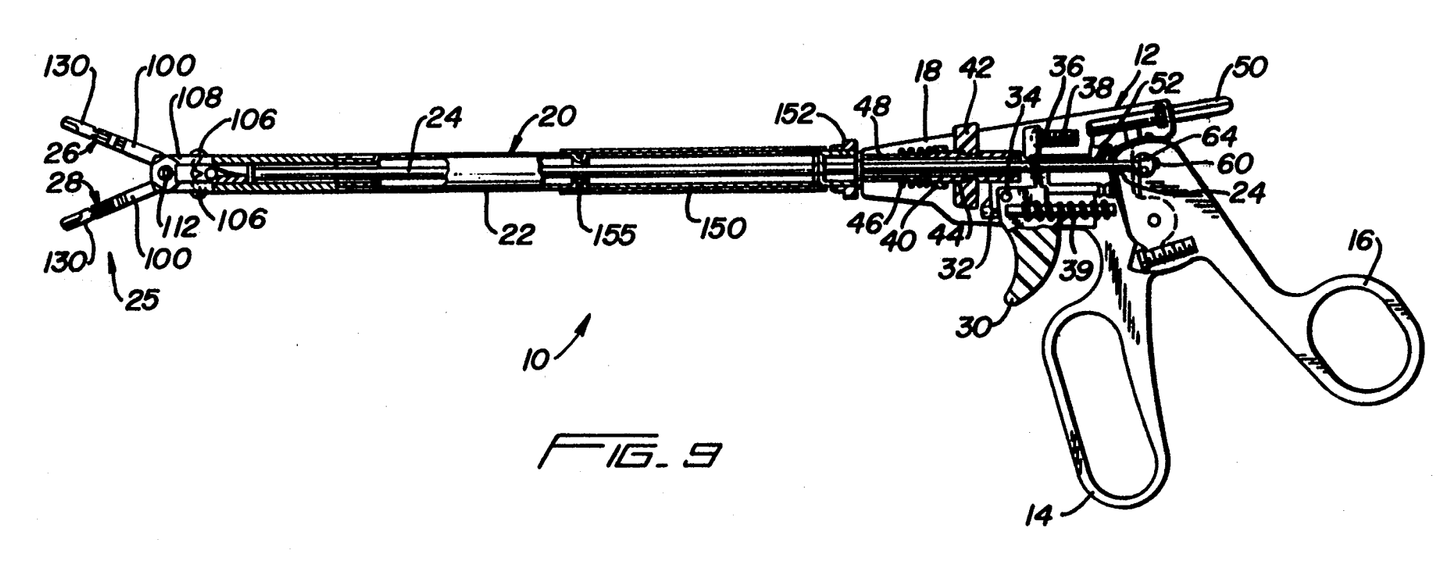
FIG. 9 is a side cross-sectional view of the surgical apparatus taken along line 9—9 of FIG. 1, with the articulable jaws in an open position corresponding to the housing tube being disposed in a proximal position.

Tubular housing 150 is adapted and configured for moving between a distal position, best seen in FIGS. 1 and 10, enclosing the opposed jaw members 26 and 28, and a proximal position adjacent the handle portion 12 of apparatus 10, as shown in FIG. 9. An annular ring 155 is provided on the endoscopic portion 20 of apparatus 10 spaced from the handle portion 12 thereof for maintaining a seal between the tubular housing 150 and the outer tube 22 of endoscopic portion 20. Although tubular housing 150 is shown as being coaxially movable with respect to the endoscopic portion 20, it will be readily understood by those skilled in the art that tool mechanism 25 can be coaxially moveable relative to endoscopic portion 20 for deploying jaw members 26 and 28 from their contracted position.

Figure 13:
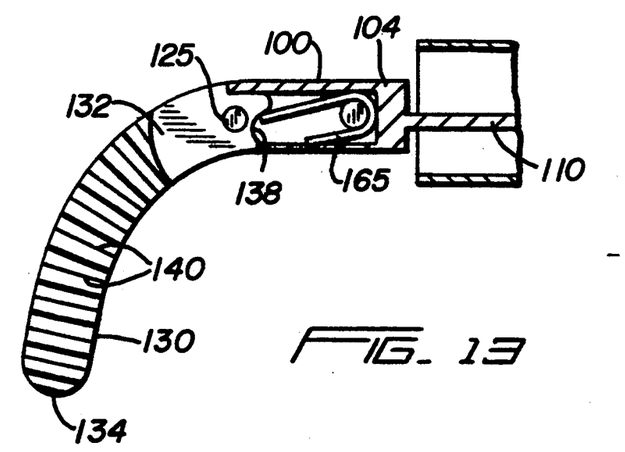
FIG. 13 is a side elevational view, partially cut-away, of another embodiment of an articulable jaw member in a fully deployed position.
Figure 14:
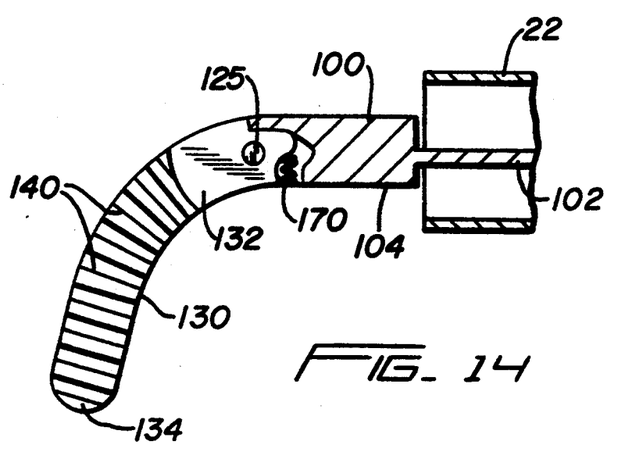
FIG. 14 is a side elevational view, partially cut-away, of yet another embodiment of an articulable jaw member in a fully deployed position.

As stated briefly above, a biasing member is associated with each of the jaws 26 and 28 for maintaining them in their deployed positions. As illustrated in Fig. 12, the biasing member comprises a cylindrical leaf spring 160 which may be formed from a shape memory alloy, comprising for example, a composition of nickel and titanium (such a composition is available from Raychem Corp., Menlo Park, Calif. under the trade name TINEL). Leaf spring 160 is maintained within the body 118 of the proximal section 100 of each of the jaws 26 and 28, and is cooperative with the notched region 138 in the distal section 130 of each of the jaws 26 and 28. Alternatively, the distal section 130 of each of the articulating jaw members 26 and 28 can be biased into a deployed position by other means including a looped torsion spring 165 which is illustrated in FIG. 13, or a coiled spring 170 which is shown in FIG. 14.

Figure 16:
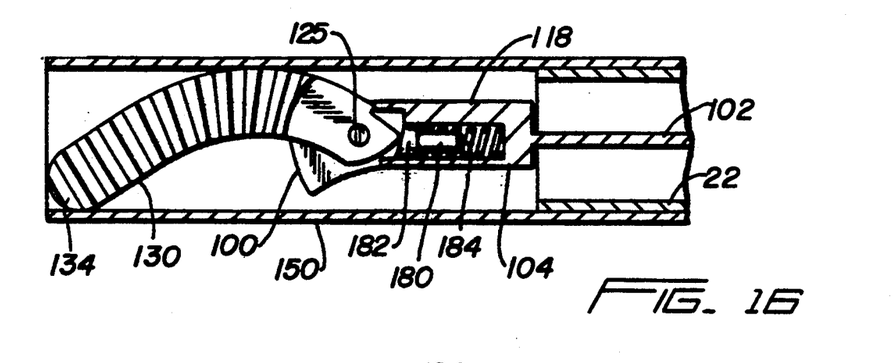
FIG. 16 is a side elevational view, partially cut-away, of still another embodiment of an articulable jaw member in a contracted position.
Figure 17:
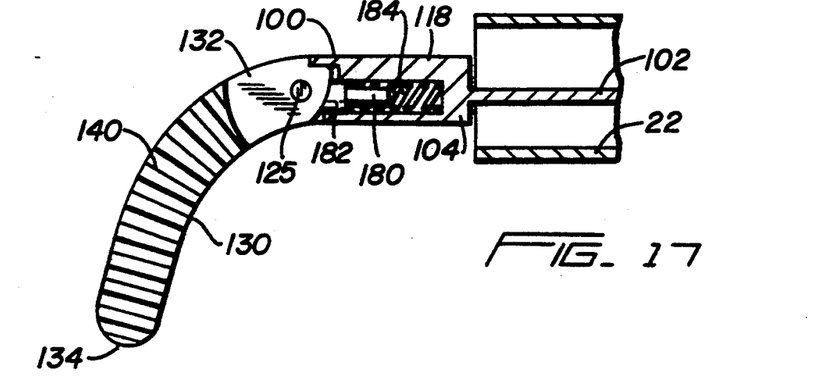
FIG. 17 is a side elevational view, partially cut-away, of the articulable jaw member of FIG. 16 in a fully deployed position.

Turning to FIGS. 16 and 17, yet another embodiment of the articulable jaw structure of the subject invention is illustrated which comprises a longitudinal plunger 180 having a distal wedge section 182. Plunger 180 is biased by a coiled spring 184 and housed within the body 118 of the clevis portion 104 of proximal section 100. As the plunger 180 is urged in a distal direction under the influence of coiled spring 184, wedge section 182 frictionally maintains the distal section 130 of each of the articulating jaw members 26 and 28 of tool mechanism 25 in their contracted position disposed within the tubular housing 150.

In use, tool mechanism 25 is introduced to the operative site by positioning tubular housing 150 over tool mechanism 25 and inserting the tubular housing 150 and the tool mechanism 25 into a trocar housing. Thereupon, the annular sleeve 152 which is formed at the proximal end of tubular housing 150 engages an annular valve seat defined at the entrance of the trocar into which it is inserted, trapping the tubular housing 150 and prohibiting its movement, while permitting the endoscopic portion 20 to continue to pass therethrough.

Once the distal end of endoscopic portion 20 has traversed the entire length of the cannula, the articulable jaw members 26 and 28 relax from their contracted position as the biasing spring urges the distal portion 130 of each of the jaws 26 and 28 into their deployed position.

Figure 18:
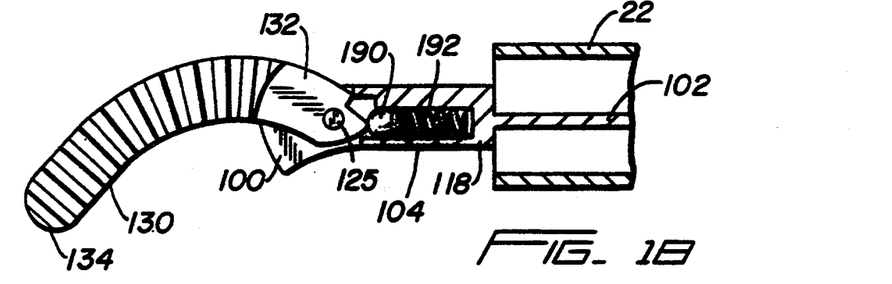
FIG. 18 is a side elevational view, partially cut-away, of yet another embodiment of an articulable jaw member in a contracted position.
Figure 19:
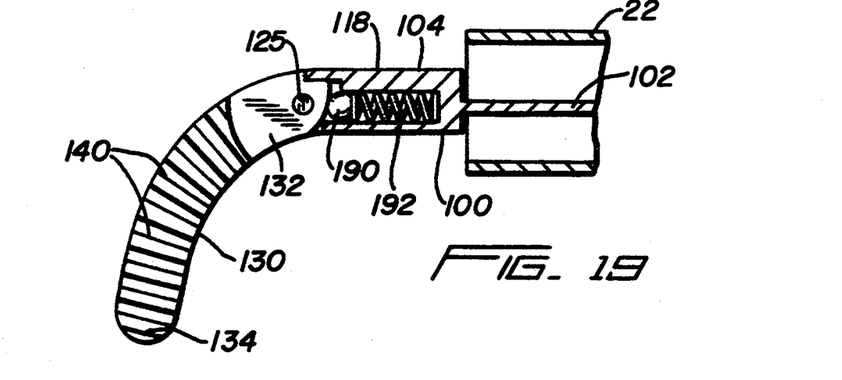
FIG. 19 is a side elevational view, partially cut-away, of the articulable jaw member of FIG. 18 in a fully deployed position.

Referring now to FIGS. 18 and 19, still another embodiment of the articulating jaw structure of the subject invention is illustrated which comprises a spherical member 190 biased by a coiled spring 192 and housed within the body 118 of the clevis portion 104 relative to the longitudinal axis thereof. In the contracted position of FIG. 18, a portion of the proximal end of distal jaw section 130 is frictionally engaged in an over center configuration by spherical member 190 as it is biased in a distal direction under the influence of coiled spring 192, releasably locking distal section 130 in its contracted position. Once introduced through a trocar or cannula device, the user may simply shift the apparatus so as to jar the distal section 130 of each of the articulating jaws 26 and 28, enabling distal section 130 to overcome the frictional over center contact between the proximal end portion thereof and the spherical member 190. Consequently, in this embodiment of tool mechanism 25, the need to employ external retaining means such as the tubular housing 150 is obviated.

While the subject invention has been described with respect to a preferred embodiment, it is apparent that changes and modifications may be made thereto without departing from the spirit or scope of the invention as defined by the appended claims.

What is claimed is:

1. A surgical apparatus comprising:
   a) a handle portion;
   b) an endoscopic portion extending from said handle portion; and
   c) a tool assembly operatively associated with a distal end of said endoscopic portion and including a pair of opposed cooperating jaw members, each of said jaw members having first and second relatively articulatable sections movable between a first position and a second position wherein said first and second sections together define a contact plane, said first section of each jaw member defining a proximal section having a fixed orientation with respect to said second section, and each of said jaw members including means for biasing said second section thereof into said second position.

2. A surgical apparatus as recited in claim 1, further comprising means for selectively maintaining said jaw members in said first position.

3. A surgical apparatus as recited in claim 2, wherein said maintaining means comprises a tubular housing telescopically associated with said endoscopic portion and movable along a longitudinal axis thereof between a proximal position spaced from said jaw members and a distal position substantially enclosing said jaw members to maintain said relatively articulatable jaw sections in said first position.

4. A surgical apparatus as recited in claim 2, wherein said maintaining means comprises a spring biased member engageable in an over center configuration with a portion of said second articulable section.

5. A surgical apparatus as recited in claim 1, further comprising means for moving said cooperating jaw members between an open position and a closed position.

6. A surgical apparatus as recited in claim 1, wherein said first and second relatively articulatable sections of each of said jaw members are normally biased in said second position.

7. A surgical apparatus as recited in claim 1, wherein said jaw members define an arcuate jaw configuration in said second position.

8. A surgical apparatus as recited in claim 1, wherein said jaw members define an angular jaw configuration in said second position.

9. A surgical apparatus as recited in claim 1, wherein said opposed cooperating jaw members are normally biased in said open position.

10. A surgical apparatus as recited in claim 1, wherein said biasing means comprises a spring selected from a group consisting of an elongated leaf spring, a looped torsion spring, and a coiled spring.

11. A surgical apparatus as recited in claim 1, wherein said biasing means comprises a wedge member frictionally engageable with said second articulatable section.

12. A surgical apparatus as recited in claim 1, wherein said biasing means comprises a spring member formed of a shape memory alloy.

13. A surgical apparatus as recited in claim 1, further comprising means for rotating said jaw members relative to said handle portion.

14. A surgical apparatus as recited in claim 1, further comprising electrocautery means associated with said handle portion for performing electrocauterization at said tool assembly.

15. A surgical apparatus as recited in claim 1, further comprising means associated with said handle portion for maintaining said opposed cooperating jaw members in said closed position.

16. A surgical apparatus as recited in claim 1, further comprising seal means associated with said endoscopic portion for inhibiting the egress of fluids.

17. A surgical apparatus as recited in claim 1, wherein said first section is distal of said second section and includes a generally serrated contact surface.

18. A surgical apparatus comprising:
   a) a handle portion;
   b) an endoscopic portion defining a longitudinal axis extending from said handle portion;
   c) a tool assembly operatively associated with a distal end of said endoscopic portion and including a pair of opposed cooperating jaw members, each of said jaw members having at least one articulating section movable between a first position and a second position;
   d) means associated with said endoscopic portion movable along said longitudinal axis thereof between a proximal position spaced from said jaw members and a distal position substantially enclosing said jaw members and maintaining said at least one articulating section in said first position; and
   e) means for moving said jaw members between an open position and a closed position.

19. A surgical apparatus as recited in claim 18, wherein said least one articulating section of each of said jaw members is normally biased in said second position.

20. A surgical apparatus as recited in claim 18, wherein said jaw members define an arcuate jaw configuration in said second position.

21. A surgical apparatus as recited in claim 18, wherein said jaw members define an angular jaw configuration in said second position.

22. A surgical apparatus as recited in claim 18, wherein said opposed jaw members are normally biased in said open position.

23. A surgical apparatus as recited in claim 18, wherein each of said jaw members includes a first section defining a distal section and a second proximal section fixed relative to said first section.

24. A surgical apparatus as recited in claim 23, wherein each of said jaw members includes means for biasing said second section thereof in said second position.

25. A surgical apparatus as recited in claim 24, wherein said biasing means comprises a spring selected from a group consisting of an elongated leaf spring, a looped torsion spring, and a coiled spring.

26. A surgical apparatus as recited in claim 24, wherein said biasing means comprises a spring member formed from a shape memory alloy.

27. A surgical apparatus as recited in claim 18, further comprising means for rotating said jaw members relative to said handle portion.

28. A surgical apparatus as recited in claim 18, further comprising electrocautery means associated with said handle portion for performing electrocauterization at said tool assembly.

29. A surgical apparatus as recited in claim 18, further comprising means associated with said handle portion for selectively maintaining said opposed cooperating jaw members in said closed position.

30. A surgical apparatus as recited in claim 18, further comprising seal means associated with said endoscopic portion for inhibiting egress of fluid.

31. Tool mechanism for use with endoscopic surgical instrumentation comprising, a pair of cooperating jaw members each having proximal and distal relatively articulatable portions movable between a contracted position and a deployed position wherein said proximal and distal portions together define a contact plane, and including means for facilitating relative movement of said jaw members between an open and closed position, and means for biasing said proximal and distal portions of each of said jaw members into said deployed position.

32. Tool mechanism as recited in claim 31, wherein said jaw members define an arcuate configuration in said deployed position.

33. Tool mechanism as recited in claim 31, wherein said jaw members define an angular configuration in said deployed position.

34. Tool mechanism as recited in claim 31, further comprising means for maintaining said proximal and distal portions of each of said jaw members in said contracted position.

35. Tool mechanism as recited in claim 34, wherein said maintaining means comprises a spring biased member engageable with said distal portion of each of said jaw members.

36. Tool mechanism as recited in claim 35, wherein said spring biased member comprises a spherical structure.

* * * * *